(12) United States Patent
Johnson et al.

(10) Patent No.: US 8,551,171 B2
(45) Date of Patent: Oct. 8, 2013

(54) METHODS OF STABILIZING THE SACROILIAC JOINT

(75) Inventors: Donald Johnson, Isle of Palms, SC (US); Daniel Butler, Summerville, SC (US)

(73) Assignee: Globus Medical, Inc., Audubon, PA (US)

( * ) Notice: Subject to any disclaimer, the term of this patent is extended or adjusted under 35 U.S.C. 154(b) by 1385 days.

(21) Appl. No.: 11/871,621

(22) Filed: Oct. 12, 2007

(65) Prior Publication Data

US 2009/0099610 A1  Apr. 16, 2009

(51) Int. Cl.
  *A61F 2/44* (2006.01)
  *A61B 17/88* (2006.01)
  *A61B 17/86* (2006.01)

(52) U.S. Cl.
  USPC ........ 623/17.11; 606/279; 606/326; 606/327; 606/313

(58) Field of Classification Search
  USPC ........ 623/17.11–17.16; 606/63–68, 86 R, 96, 606/102, 104, 279, 300–321, 325–329; 411/29, 38, 43
  See application file for complete search history.

(56) References Cited

U.S. PATENT DOCUMENTS

| | | | |
|---|---|---|---|
| 5,334,205 A * | 8/1994 | Cain | 606/96 |
| 7,128,760 B2 * | 10/2006 | Michelson | 623/17.15 |
| 2002/0087161 A1 * | 7/2002 | Randall et al. | 606/73 |
| 2004/0097927 A1 * | 5/2004 | Yeung et al. | 606/61 |
| 2005/0177167 A1 * | 8/2005 | Muckter | 606/73 |
| 2008/0009861 A1 * | 1/2008 | Stark | 606/61 |
| 2009/0024174 A1 * | 1/2009 | Stark | 606/321 |
| 2009/0259261 A1 * | 10/2009 | Reiley | 606/329 |

* cited by examiner

*Primary Examiner* — Matthew Lawson

(57) ABSTRACT

Methods of stabilizing the sacroiliac joint by placing an expandable device in the joint to generate laterally opposing forces against the iliac and sacral surfaces of the SI joint to securely seat the device in a plane generally parallel to the SI joint. The expandable device is coated with or otherwise contains a bone material to promote fusion of the joint. The expandable device used in methods of the present invention can be, for example, an expandable cage, a balloon, a balloon-expandable stent or a self-expanding stent.

13 Claims, 14 Drawing Sheets

METHODS OF STABILIZING THE SACROILIAC JOINT

TECHNICAL FIELD

The present application is directed to various methods for stabilizing the sacroiliac joint including via fusing the joint.

SUMMARY OF THE INVENTION

The sacroiliac (SI) joint is a diarthrodial joint that joins the sacrum to the pelvis. In this joint, hyaline cartilage on the sacral side moves against fibrocartilage on the iliac side. The joint is generally C shaped with 2 lever arms that interlock at the second sacral level. The joint contains numerous ridges and depressions, indicating its function for stability more than motion. In fact, the SI joint's main function appears to be providing shock absorption for the spine through stretching in various directions. Stability in the SI joint is provided by the large ridges present in the joint and by the presence of generously sized ligaments, which offer resistance to shear and loading. The deep anterior, posterior, and interosseous ligaments resist the load of the sacrum relative to the ilium and the more superficial ligaments, such as the sacrotuberous ligament react to dynamic motions.

The human spinal column is configured so that the total weight of the upper body rests on the two small SI joints at the juncture of the sacrum and ilia. The stress placed on this area in the upright position makes the lower back susceptible to injury. In fact, one of the most common causes of problems at the SI joint is an injury. The force from such an injury can strain the ligaments around the joint potentially causing tearing which can lead to hypermobility in the joint. Such hypermobility can eventually lead to wear and tear of the joint and pain from degenerative arthritis. Injuries can also cause direct injury of the articular cartilage lining the joint, which too, over time, can lead to degenerative arthritis in the joint.

In some patients, SI joint pain occurs because of an abnormality of the sacrum bone itself. Before birth, several vertebra fuse together to form the sacrum but in some patient populations, the bones that constitute the sacrum never fuse together. In these cases, two or more of the vertebra that should fuse together remain separated, which can give rise to problems with the SI joint.

Furthermore, women may be at risk for developing SI joint problems later in life due to childbirth since the long dorsal sacroiliac ligament can become stretched in periods of such reduced lumbar lordosis (i.e. pregnancy). Specifically, During pregnancy, hormones are released that allow the connective tissues in the body to relax. The relaxation is necessary so that during delivery, the female pelvis can stretch enough to allow birth. However, this stretching can cause changes to the SI joints, making them hypermobile. Over a period of years, these changes can eventually lead to wear-and-tear arthritis. As would be expected, the more pregnancies a woman has, the higher her chances of SI joint problems.

Surgery on the SI joint usually consists of a fusion of the joint. An SI joint fusion is performed by first making an incision over the SI joint in the lower back. The joint is opened so the surgeon can visualize the iliac and sacral surfaces of the SI joint. Once the joint surfaces are in clear view, the articular cartilage lining the joint is removed from both surfaces. The bone surfaces are then held together until they actually heal together, or fuse. To hold the bones together, the surgeon will usually insert several metal screws across the joint or a bone plate. This historically has been a large surgical procedure without great success.

Therefore, there is a need in the art for a minimally invasive device that provides for long term joint stability.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

SUMMARY OF THE INVENTION

In an embodiment, the present invention provides a method of stabilizing a sacroiliac joint in a patient in need thereof. The method comprises providing a device that comprises an expandable body defining a cavity and at least one opening in communication with (i) the cavity and (ii) the outer surface of the body. The expandable body is generally fabricated from a material that is rigid enough to withstand the compressive and torsional forces accepted by the SI joint but flexible enough to assume both an unexpanded configuration in a non-deployed state and a radially expanded configuration in a deployed state. The method further comprises inserting the device into the sacroiliac joint. The device can be inserted percutaneously or via open surgery. Once properly positioned, the method further comprises expanding the expandable body to engage the sacroiliac joint to securely seat the expandable device in the sacroiliac joint. By being securely seated in the sacroiliac joint, the device is not readily displaced by normal bodily movement. The method further comprises providing a bone material in or one the expandable body of the device to permit fusion of the sacroiliac joint.

The methods of the present invention can be used to treat dysfunction of the SI joint resulting in destabilization, such as hypermobility, of the joint. Such SI joint dysfunction can be can be caused by disease, age, injury or other factors.

DETAILED DESCRIPTION OF THE INVENTION

In general, the present invention provides methods of stabilizing the sacroiliac joint in a patient in need thereof using a device having an expandable portion that engages the sacral and iliac surfaces of the sacroiliac joint. Specifically, referring to FIG. 1, the methods involve generating laterally opposing forces against the iliac and sacral surfaces of the SI joint to securely seat a device 10 in a plane generally parallel to the SI joint. Prior methods, in contrast, involved disposing a bone screw perpendicular to the joint to direct compressive forces against the iliac and sacral surfaces to draw the surfaces closer together. The expandable portion of devices used in the methods of the present invention is either coated with or otherwise contains a bone material, such as bone graft or a substrate containing a bone morphogenic protein, to facilitate fusion of the joint. By stabilizing the sacroiliac joint, the methods of the present invention eliminate or reduce motion across the joint and fuse the sacrum and ilium bones at the SI joint. The device used in methods of the present invention can include any biocompatible devices which have an expandable portion that can assume both an unexpanded and radially expanded position and that are sized to fit in, but not necessarily expand, the SI joint in a fully deployed position.

Figure 1:
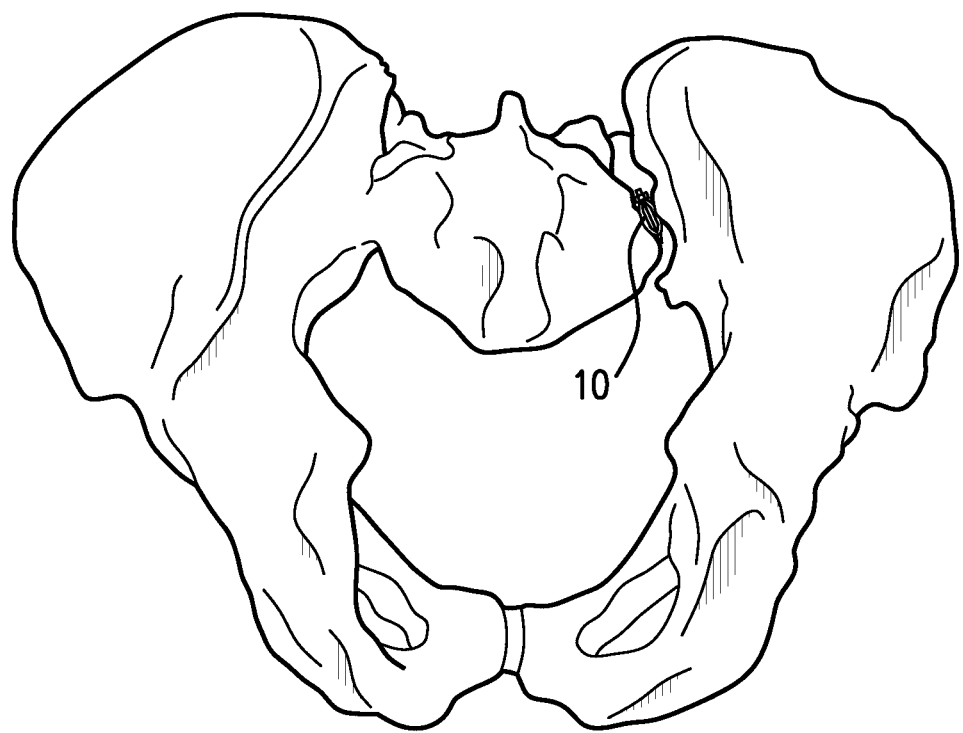
FIG. 1 is a schematic illustration of a device of the present invention positioned in the sacroiliac joint in an expanded, deployed configuration.
Figure 2:
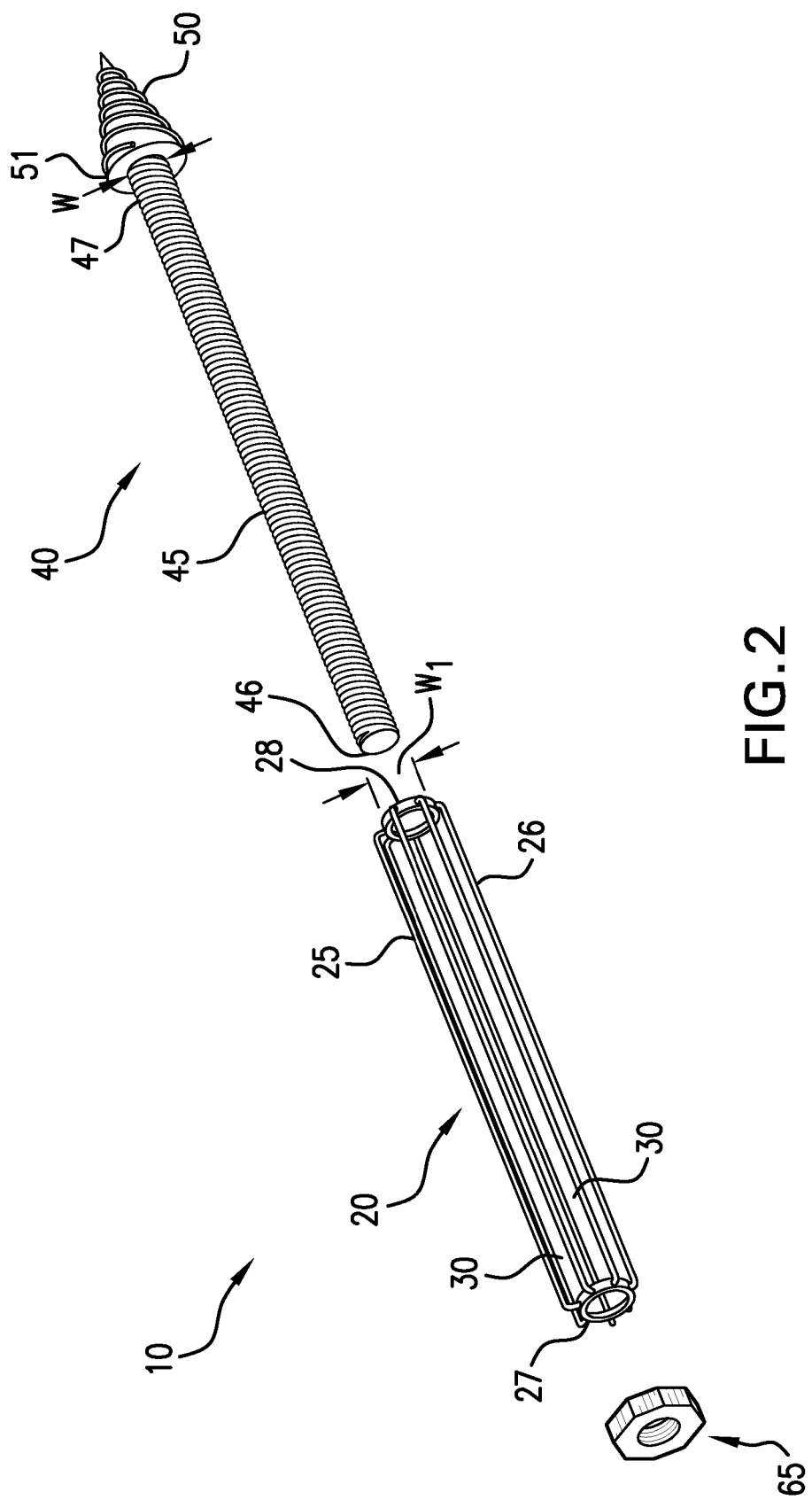
FIG. 2 is an exploded view of a device according to an embodiment of the present invention.

For example, referring to FIG. 2, in an embodiment, a device 10 that can be used in methods of the present invention comprises an expandable body 20 defining a cavity 25. In this embodiment, expandable body 20 comprises a plurality of strips 26 that axially extend from a proximal end 27 to a distal end 28 of body 20 and that are capable of yielding laterally when compressed axially. Preferably, strips 26 are uniformly circumferentially spaced apart. As seen in FIG. 1, the plurality of strips 26 define a plurality of axially extending openings or slits 30 between adjacent ones of the plurality of strips 26, such openings or slits 30 being in fluid communication with cavity 25. However, other embodiments of body 20 are also contemplated where body 20 defines at least one opening extending from the outer surface of body 20 to the inner surface and therefore in communication with cavity 25 as well as the exterior of body 20. Cavity 25 allows for receipt of a bone material and openings 30 provide a pathway by which bone ingrowth can be achieved. In other words, when device 10 is in a fully deployed position, expandable body 20 allows for bony ingrowth through openings 30 to cavity 25, when the cavity is filled with a substance that encourages bone growth.

Figure 3:
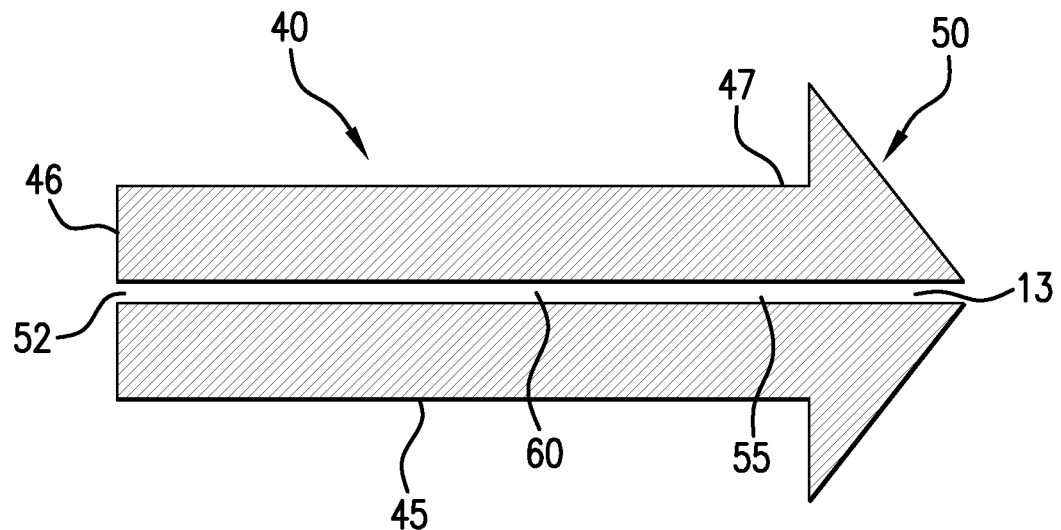
FIG. 3 is a cross-sectional view of a screw of a device according to an embodiment of the present invention.

In this embodiment, device 10 further comprises a screw 40 comprising a shaft 45 having a proximal end 46 and a distal end 47 and upon which expandable body 20 is mounted during use. In the embodiment illustrated in FIG. 2, shaft 45 is fully threaded. However, in other embodiments, shaft 45 can be partially threaded. Screw 40 further comprises a pointed, cutting distal tip 50 extending from the distal end of shaft 45. Distal tip 50 has a proximal face 51 that has a width W greater than the width $W_1$ of the distal end of shaft 45 so as to accept the axially compressive forces of expandable body 20 when device 10 is being deployed. Referring to FIG. 3, in this embodiment, proximal end 46 of shaft 45 defines a proximal opening 52, distal end 47 defines a distal opening 55, and a hollow channel 60 extends between proximal end 46 and distal end 47 and is in fluid communication with proximal opening 52 and distal opening 55. Distal tip 50 also comprises a channel 13 in registration with channel 60 and in fluid communication with distal opening 55 of shaft 45. Both channels 60 and 13 are sized to accommodate a guidewire, which can be used during insertion of device 10 into the patient's body.

Figure 4:
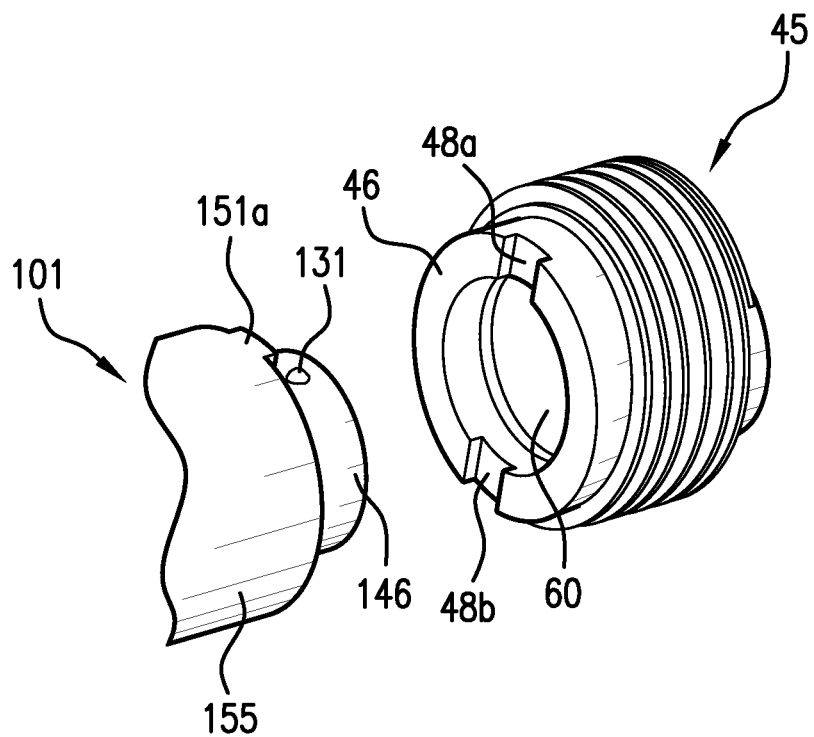
FIG. 4 is a fragmentary perspective view of a screw of a device according to an embodiment of the present invention and a fragmentary perspective view of an installation tool that can be used to rotate the screw.

Proximal end 46 of shaft 45 can be configured to accept a distal end of a driving tool to rotationally drive screw 40 through bone and into the sacroiliac joint. For example, referring to FIG. 4, a driving tool 101 can be used which has a larger cylindrical section 155 with opposing mating flanges 151a and 151b (not shown) and a smaller diameter cylindrical extension 146 extending from larger section 155. A spring loaded ball detent 131 can be disposed on the distal end of extension 146. Proximal end 46 of shaft 45 can define a pair of opposing slots 48a and 48b, configured to receive opposing mating flanges 151a and 151b on driving tool 101. Further, channel 60 of device 10 can be sized to frictionally engage cylindrical extension 146 of driving tool 101. At the appropriate point in the surgical procedure when the device 10 is ready to be installed, cylindrical extension 146 can be inserted into channel 60 such that ball detent 131 resides in channel 60. Mating flanges 151 and 152 are aligned with slots 48 and the device can then be screwed into place. Of course, other means of engaging a driving tool with the proximal end of screw 40 can also be used such as other male/female connections; threadable engagement; and/or interference or frictional fit.

Figure 5:
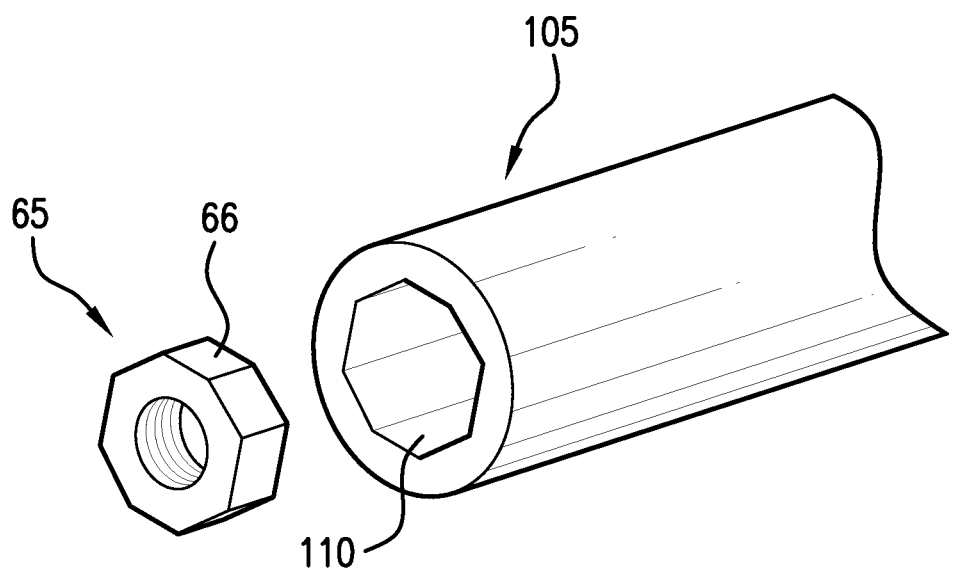
FIG. 5 is a perspective view of a locking nut of a device according to an embodiment of the present invention and a fragmentary perspective view of an installation tool that be used to rotate the locking nut.

Referring back to FIG. 2, this embodiment of device 10 also includes a locking nut 65 to threadably engage shaft 45 of screw 40. Locking nut 65 can also be configured to accept the distal end of a driving tool to tighten nut onto shaft 45. For example, referring to FIG. 5, locking nut 65 can have a hexagonal shaped outer surface 66 to engage a driver tool 105 having a distal end having a complementary shaped inner surface 110.

Although in the above-described embodiments, the driving tools used to rotate the screw and nut are separate devices, a single device can be used to rotate each component. Further, although in the above-described embodiments, the devices used to rotate the screw and nut are independently actuatable since one component is held stationary while the other component is urged distally or proximally in order to expand the expandable body, in other situations it may be necessary to rotate both screw and nut simultaneously in order to advance the device in the patient's body. In such embodiments, the installation tools used to rotate the screw may be a single device that rotate the components in concert.

The components of the device can be fabricated from various materials to allow such components to operate according to their intended function. For example, the expandable body can be fabricated from any sterile, biocompatible material that is flexible enough such that it can be compressed when axial forces are applied thereto yet have sufficient compressive strength to remain in an expanded configuration when fully deployed for a long enough period of time to permit bone fusion. For example, expandable body can be fabricated from a deformable material such as a flexible metal or elastomeric polymer. Non-limiting examples of suitable materials include titanium, expandable polytetrafluorethylene (ePTFE), or polyetheretherketone (PEEK). The screw and locking nut can be fabricated from a number of sterile, biocompatible materials such as a metal, a polymeric material, or a ceramic. Non-limiting examples of a metal include stainless steel, cobalt-chrome or titanium alloys. Non-limiting examples of plastics include a blend of polycaprolactone and polyglycolide, a blend of polylactide and polyglycolide, pure polydioxanone, poly(ethylene oxide), poly(butylene terephthalate), polyorthoester, or polyhydroxybutyrate. In certain embodiments, the components of the device are fabricated from biodegradable materials such as polycaprolactone, poly (L-lactide), polyglycol, poly(D,L-lactide), poly(D,L-lactide-co-glycol), poly(D,L-lactide-cocaprtrolactone), polydioxanone, copolyoxalates and polycarbonates, such as, for example, polyglycol-co-trimethylenecarbonate and poly (glutamine-co-leucine).

Furthermore, the components of the device can be completely separate components or certain components can be integrally attached. For example, the expandable body can be fixedly attached to the distal side of the locking nut, fixedly attached to the proximal surface of the distal tip of the screw, or fixedly attached to both the distal side of the locking nut and the proximal surface of the distal tip of the screw. In other embodiments, the device can be fabricated as one single unitary piece without separable components.

Figure 6A:
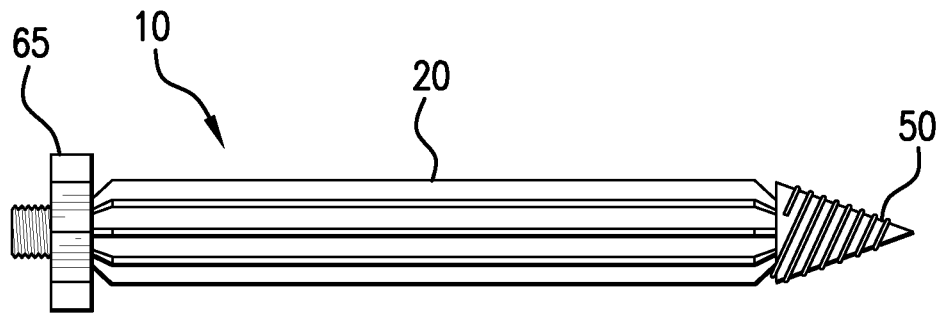
FIG. 6A is a side view of an assembled device according to an embodiment of the present invention is an unexpanded, non-deployed state.
Figure 6B:
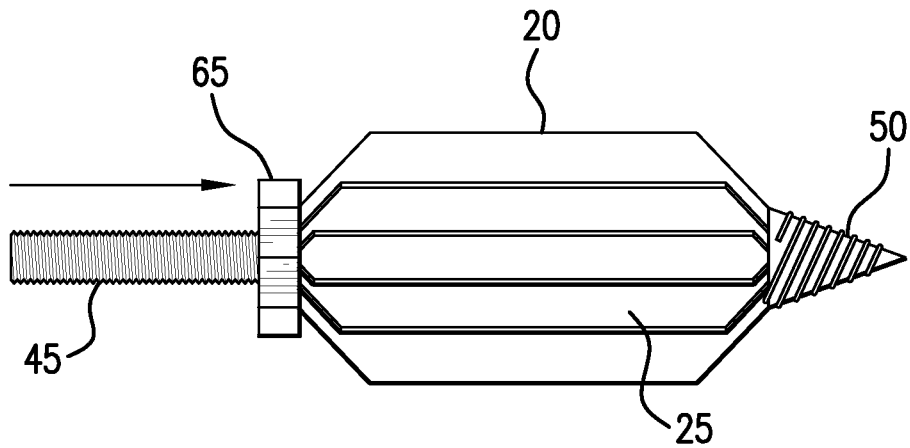
FIG. 6B is a side view of the device of FIG. 6A in an expanded state.
Figure 6C:
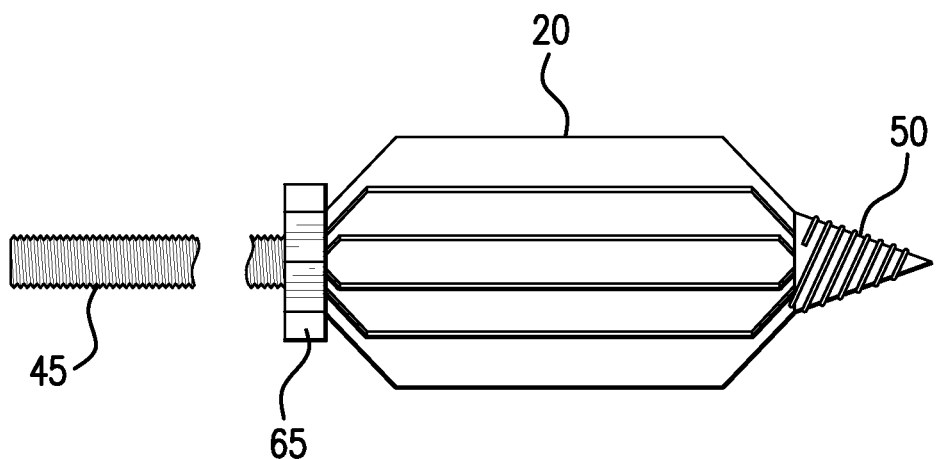
FIG. 6C is a side view of the device of FIG. 6B after a portion of the screw of the device has been cut off.

Referring to FIG. 6A, in an exemplary use of device 10, body 20 is placed onto shaft 45 of screw 40 in an unexpanded, non-deployed state. As seen in this figure, body 20 has a generally elongated cylindrical configuration in this unexpanded state. Locking nut 65 is then threaded onto shaft 45 proximal to body 20. One or more driving tools are used to rotationally drive both screw 40 and locking nut 65 into the sacroiliac joint. Referring to FIG. 6B, once device 10 reaches the proper position in the joint, screw 40 can be held stationary while locking nut 65 is rotated to move distally down shaft 45 of screw 40 in the direction of the arrow to urge body 20 against the proximally facing surface 51 of distal tip 50. Body 20 is thereby compressed and radially expands. Once in an expanded configuration, body 20 engages the sacral and iliac surfaces of the sacroiliac joint. As is seen in FIG. 6B, body 20 has a generally oblong configuration in this expanded state. Once device 10 is securely positioned, a portion of shaft 45 proximal to locking nut 65 can then be cut or broken off as shown in FIG. 6C. Either prior to or after placement of device 10 in the sacroiliac joint, a bone material can be placed in cavity 25 of body 20. Alternatively, a bone material can be pre-coated onto the outer surface of body 20. Eventually, a patient's body incorporates the bone material and device 10 becomes structurally united with the joined bones.

Figure 7A:
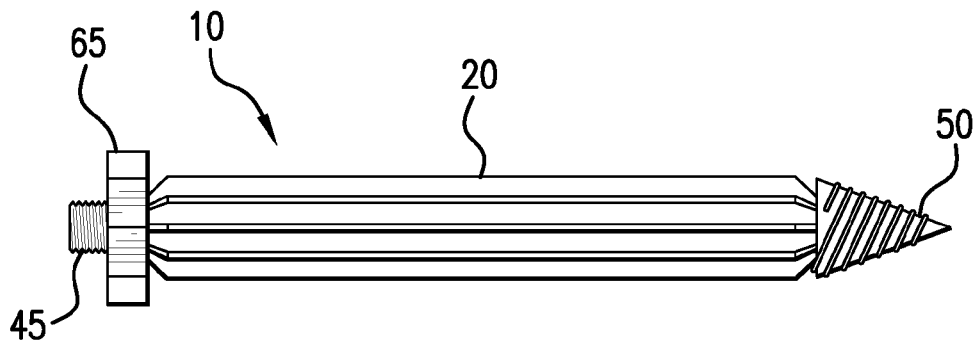
FIG. 7A is a side view of an assembled device according to an embodiment of the present invention is an unexpanded, non-deployed state.
Figure 7B:
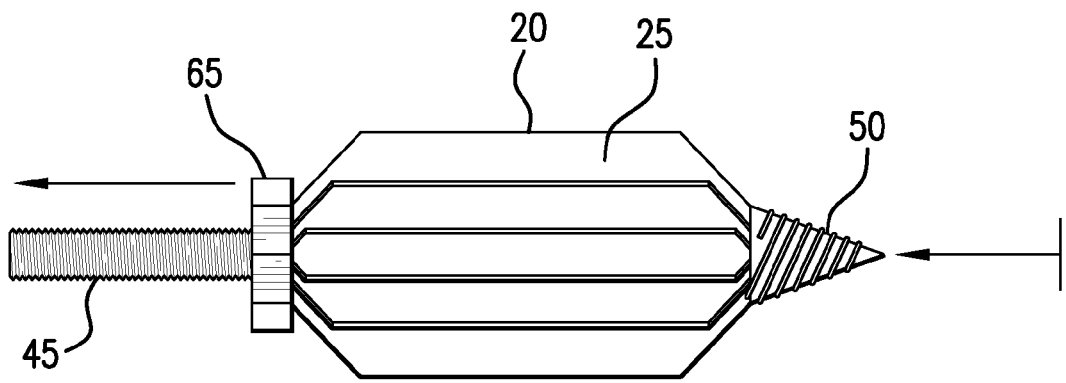
FIG. 7B is a side view of the device of FIG. 7A in an expanded state.
Figure 7C:
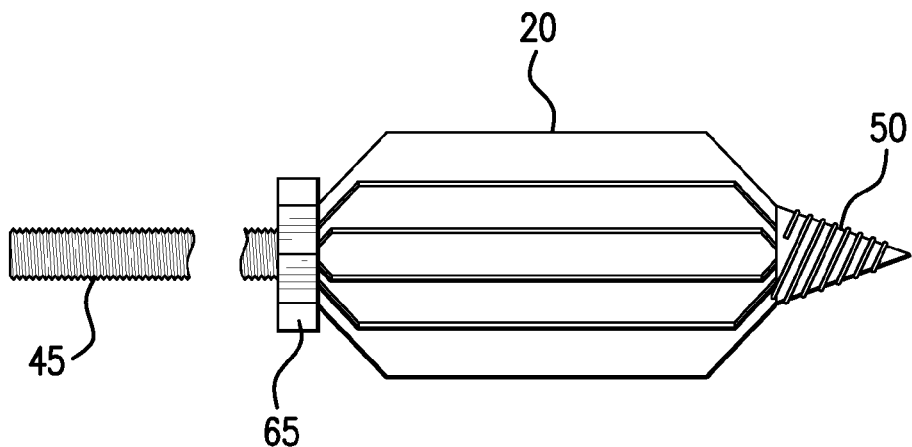
FIG. 7C is a side view of the device of FIG. 7B after a portion of the screw of the device has been cut off.

Referring to FIGS. 7A-7C, in an alternative method of installing device 10, instead of holding screw 40 stationary and rotating locking nut 65 to move distally along shaft 45, locking nut 65 can be held stationary and screw 40 rotated to move proximally in the direction of the arrow to draw expandable body 20 against locking nut 65, thereby compressing body 20 and causing its radial expansion.

Figure 8:
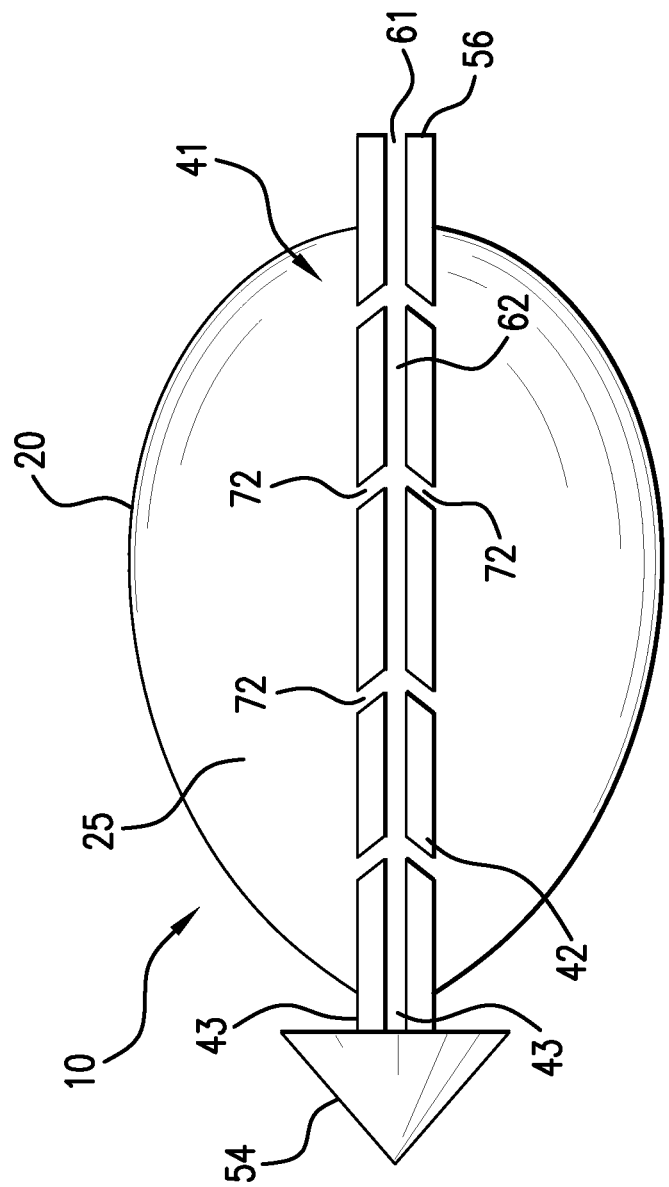
FIG. 8 is a cross-sectional view of a device according to another embodiment of the present invention in an expanded state.

Referring to FIG. 8 in another embodiment, device 10 comprises an expandable body 20 that is a balloon which defines a cavity 25. In certain embodiments, the outer surface of expandable body 20 is coated with a bone material and in other embodiments, a bone material is contained within cavity 20 of expandable body 20, in which case expandable body 20 is fabricated from a biodegradable material. Device 10 further comprises an elongate member 41 comprising a shaft 42 upon which expandable body 20 is mounted and has a proximal end 56 and a distal end 43. In certain embodiments, elongate member 41 further comprises a pointed, cutting distal tip 54 extending from distal end 43 of shaft 42 and having a closed distal end. Proximal end 56 of shaft 42 defines a proximal opening 61 and a hollow channel 62 that extends between proximal end 56 and distal end 43 and is in fluid communication with proximal opening 61. Hollow channel 62 can be sized to accommodate a guidewire, which can be used during insertion of device 10 into the patient's body. Hollow channel 62 can also be used to deliver material to cavity 25 of expandable body 20. For example, in certain embodiments, shaft 42 defines a plurality of apertures 72 in fluid communication with channel 62 at one end and in fluid communication with cavity 25 at another end. In embodiments where cavity 25 contains a bone material, apertures 72 allow for the bone material to be delivered through channel 62 into cavity 25. In embodiments where the outer surface of expandable body 20 is coated with a bone material, apertures 72 allow for an infusate material, which solely functions to inflate body 20, to be delivered through channel 62 to infuse cavity 25 and expand expandable body 20. In other embodiments, the shaft can define a lumen(s) separate than the hollow channel to deliver either an infusate or a bone material to the cavity of the expandable body.

Figure 9A:
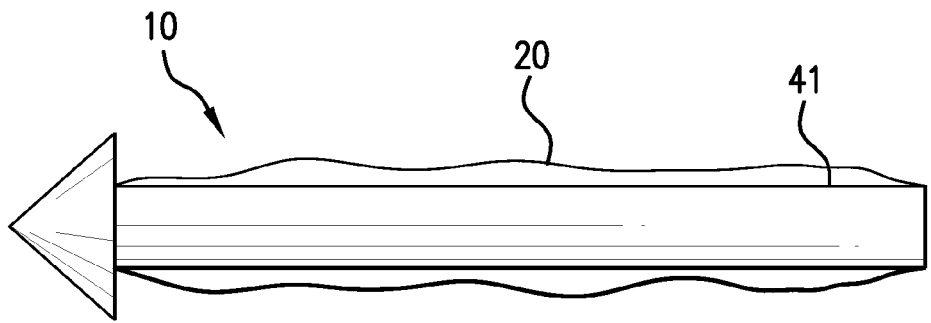
FIG. 9A is a side view of a device in an unexpanded non-deployed state according to an embodiment of the present invention.
Figure 9B:
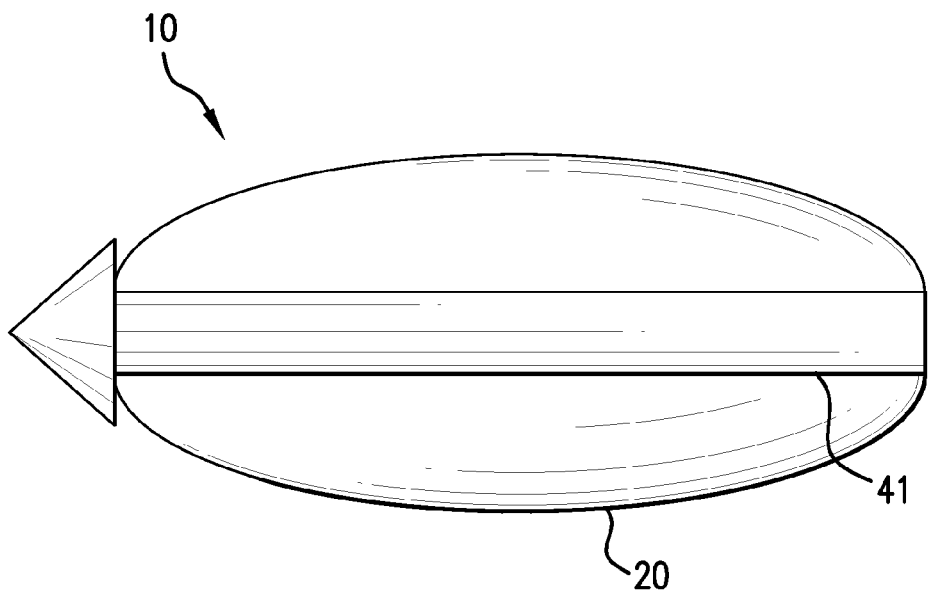
FIG. 9B is a side view of the device of FIG. 9A in an expanded state according to an embodiment of the present invention.

Referring to FIGS. 9A-9B, in an exemplary use of device 10, body 20 is disposed on shaft 42 of elongate member 41 in an unexpanded, collapsed configuration. One or more driving tools are used to rotationally drive elongate member 41 into the sacroiliac joint. Such driving tools can be similar to those described above or can have alternative designs so long as they can perform the function of delivering the device to the SI joint. In certain embodiments, once device 10 reaches the proper position in the joint, a bone material is infused through channel 62 into cavity 25 to expand body 20 such that body 20 abuts against the sacral and iliac surfaces of the SI joint. After time, expandable body 20 biodegrades, releasing the bone material contained within cavity 25. In other embodiments, the outer surface of body 20 is coated with a bone material and an infusate is infused through channel 62 into cavity 25 to inflate body 20. In an expanded deployed state, the sacral and iliac surfaces of the SI joint are exposed to the coating on body 20. In either embodiment, the SI joint is exposed to bone material facilitating fusion of the joint.

In this embodiment, the expandable body is preferably fabricated from a non-compliant material such that the material elongates upon the application of pressure and takes the shape of the areas of the SI joint in which the expandable body is placed when fully inflated. Suitable balloon materials include elastomers, such as, for example, silicone, latex, or low durometer polyurethane (for example, a durometer of about 80 A). Preferably, the expandable body, particularly in embodiments where cavity 25 is filled with bone materials but also in embodiments where the expandable body is coated with a bone material, is fabricated from a biodegradable material such as a polylactic acid polymer, a polyvinyl acetate, an acrylonitrile or other biodegradable balloon materials described in WO/2006/001009, which is incorporated by reference herein.

Figure 10A:
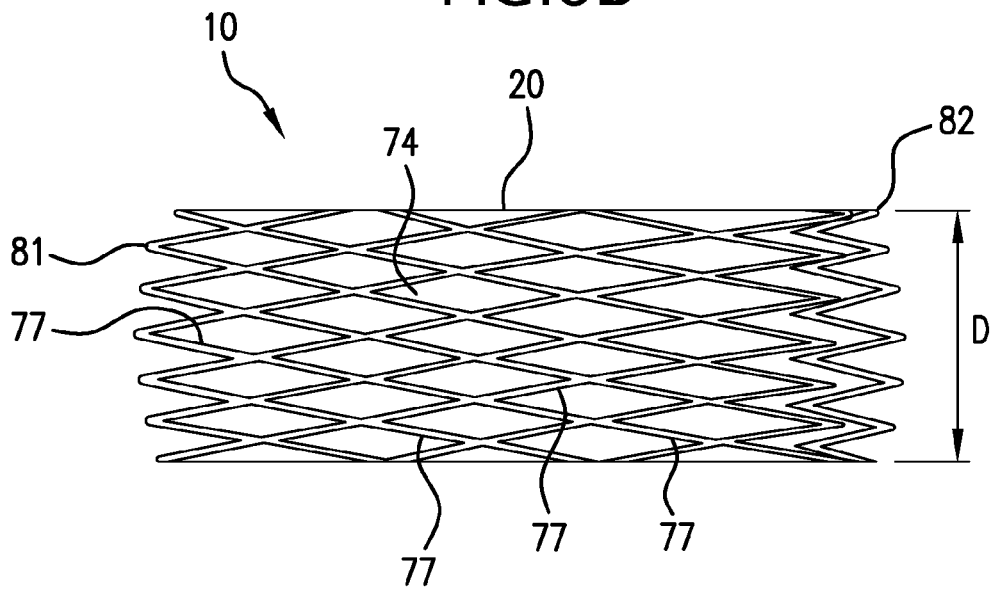
FIG. 10A is a plan view of a device in an unexpanded non-deployed state according to an embodiment of the present invention.
Figure 10B:
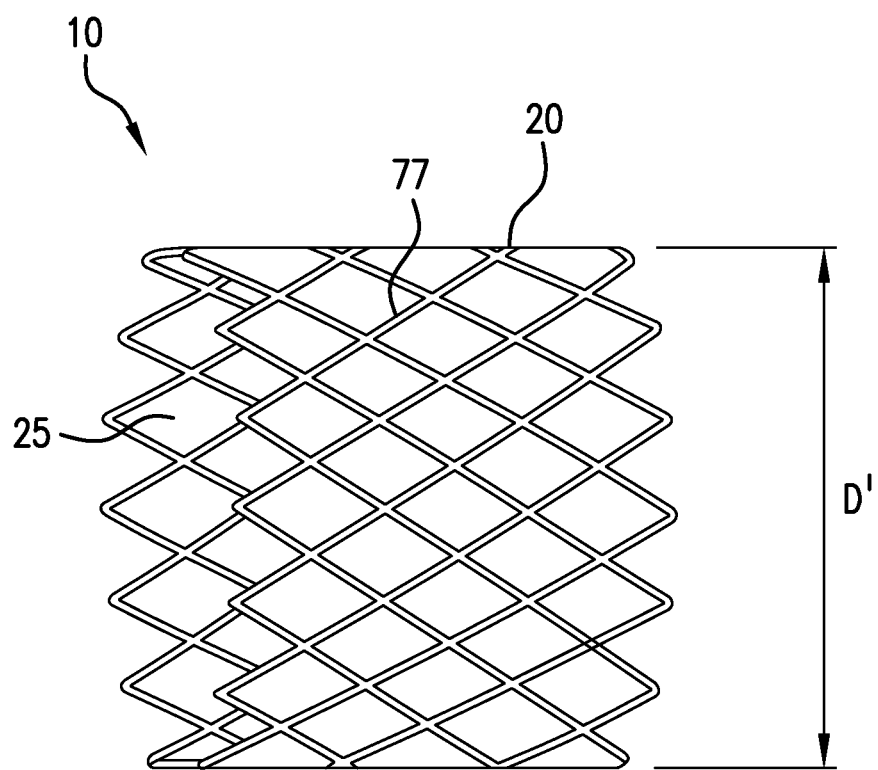
FIG. 10B is a plan view of the device of FIG. 10A in an expanded state according to an embodiment of the present invention.
Figure 11A:
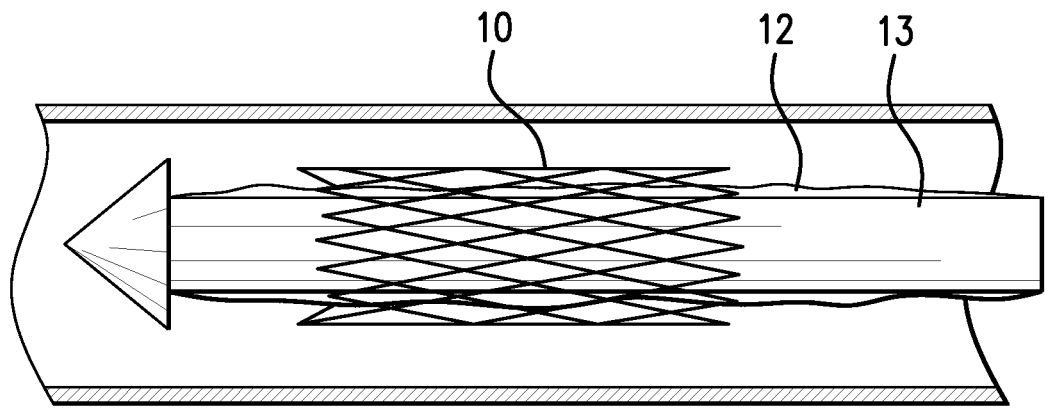
FIG. 11A is a perspective view depicting a device mounted to an elongate member in an unexpanded non-deployed state and being inserted into an SI joint according to an embodiment of the present invention.

Referring to FIGS. 10A and 10B, in other embodiments, device 10 comprises a balloon expandable stent. Specifically, device 10 comprises an expandable body 20 that has a tubular configuration similar to a stent, and which defines a cavity 25. As seen in FIG. 11A, body 20 comprises a first end 81, a second end 82 and a wall surface 74 disposed therebetween. In this embodiment, wall surface 74 is formed by a plurality of intersecting elongate members 77 but other designs are also possible as described below. Expandable body 20 assumes a first diameter D in a relaxed state and a second diameter D' upon the application of a radial force extending outwardly from the interior of cavity 25. In certain embodiments, the outer surface of expandable body 20 is coated with a bone material and in other embodiments, a bone material is contained within cavity 25 of expandable body 20.

Although in the embodiment illustrated in FIG. 10, expandable body 25 comprises a plurality of intersecting elongate members 77, in other embodiments, wall surface 74 can have a coil-like configuration, a helical configuration or other configurations common in the balloon expanding stent field including those described in U.S. Pat. No. 4,733,665, which is incorporated by reference herein. For example, one design possibility is for the expandable body of the device to be a small tube composed of collapsed metal struts linked to one another by laser or spot welding or for the expandable body to be a metal tube where the collapsed struts are carved into the tube using any of a variety of means, including laser energy. Numerous other strut designs are possible that would permit balloon expansion of expandable body 20.

Figure 11B:
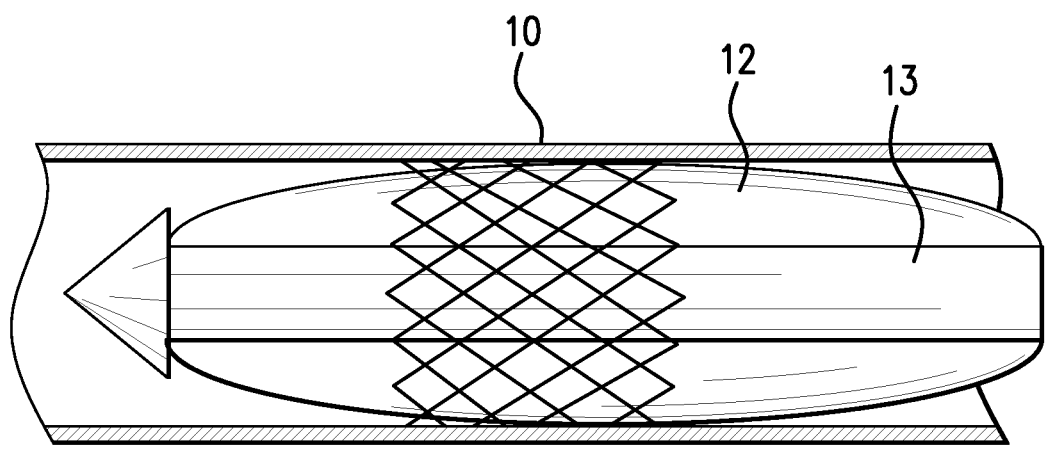
FIG. 11B is a side view of the device of FIG. 11A in an expanded state in the SI joint according to an embodiment of the present invention.
Figure 11C:
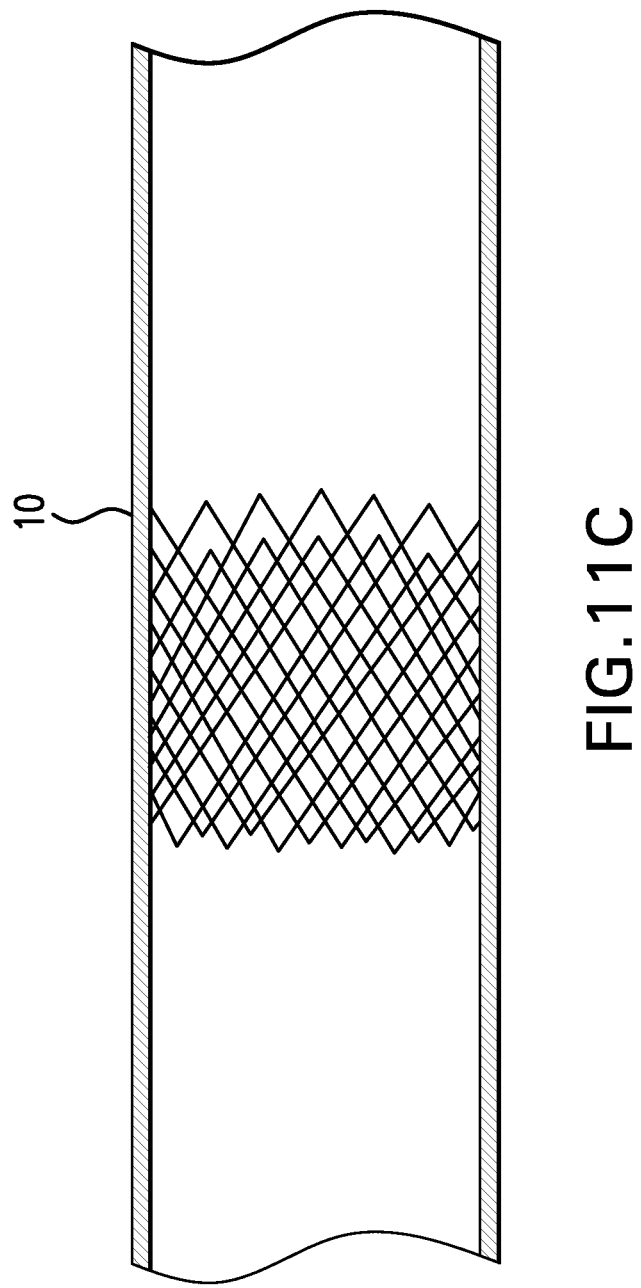
FIG. 11C is a side view of the device of FIG. 11B in an expanded deployed state in the SI joint after removal of the elongate member.

Referring to FIGS. 11A-11C, in an exemplary use of device 10, device 10 can be collapsed down onto a folded balloon 12 mounted to an elongate member 13 similar to the elongate member shown in FIG. 8. Device 10 maintains this collapsed configuration, as seen in FIG. 11A, until it is affirmatively expanded. Device 10 is inserted into the SI joint and once properly positioned, balloon 12 is inflated to an appropriate size, expanding device 12 to the desired diameter as seen in FIG. 11B. Balloon 12 is then deflated and elongate member 13 withdrawn, leaving expanded device 10 in place within the SI joint as shown in FIG. 11C. Device 10 remains in its expanded deployed state because of the deformation that was imparted to its structural elements during expansion. At any time during placement, a bone material can be inserted into cavity 25 of expandable body 20 or the outer surface of expandable body 20 can be pre-coated with a bone material. In either embodiment, the SI joint is exposed to bone material facilitating fusion of the joint.

The device can be fabricated from materials commonly used in the manufacture of balloon expandable stents such as stainless steel, polymeric or bioabsorbable materials. In preferred embodiments, the device is fabricated from a biodegradable material such as, for example, copolymers of L-lactide and/or ϵ-caprolactone.

Figure 12A:
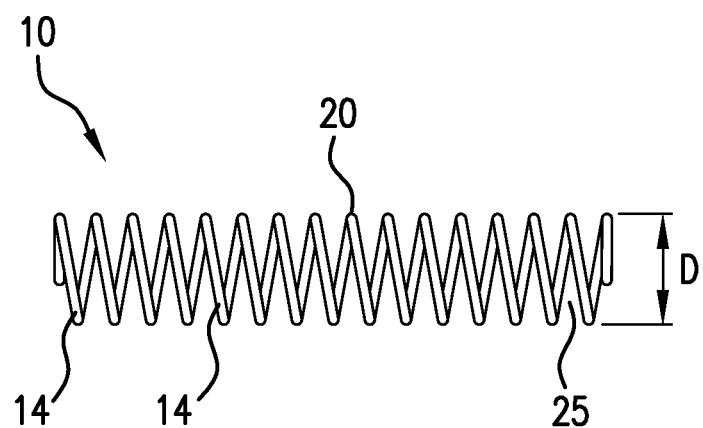
FIG. 12A is a plan view of a device in an unexpanded non-deployed state according to an embodiment of the present invention.
Figure 12B:
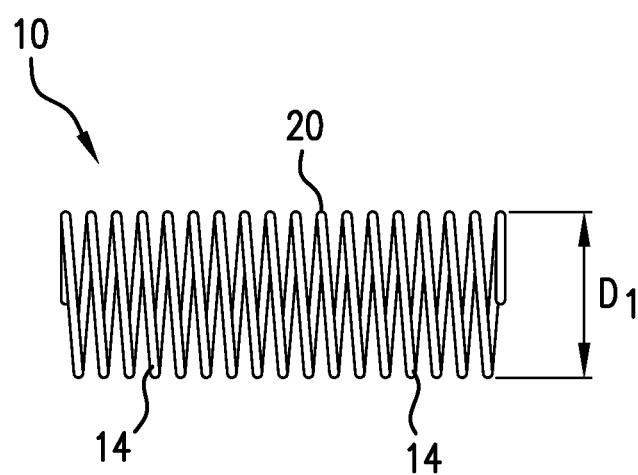
FIG. 12B is a plan view of the device of FIG. 12A in an expanded state according to an embodiment of the present invention.

Referring to FIGS. 12A and 12B, in another embodiment, device 10 is a self-expanding stent. Specifically, device 10 comprises a self-expanding body 20 that is a tubular shaped coil of wire having a plurality of helical turns 14 and which defines a cavity 25. In this embodiment, body 20 is fabricated from a shape memory alloy that can be manufactured according to well known principles so that when heated to its transition temperature, it assumes a diameter that is approximately equal to that of the SI joint so that device 10 can be securely fitted into the joint. Specifically, expandable body 20 assumes a first diameter D in a relaxed state and a second diameter D' upon radial expansion. Therefore, in contrast to the balloon-expandable device described above, device 10 of this embodiment is formed to assume a pre-determined diameter.

Figure 13A:
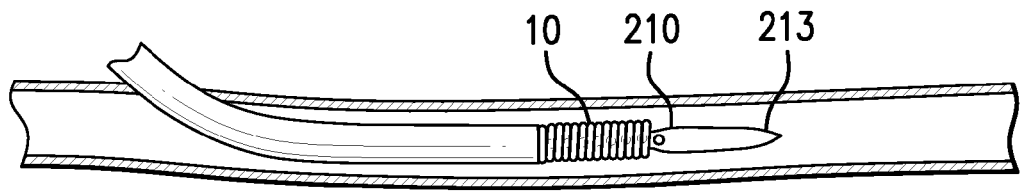
FIG. 13A is a side view depicting a device mounted to an elongate member in an unexpanded non-deployed state as it is being inserted into the SI joint according to an embodiment of the present invention.
Figure 13B:
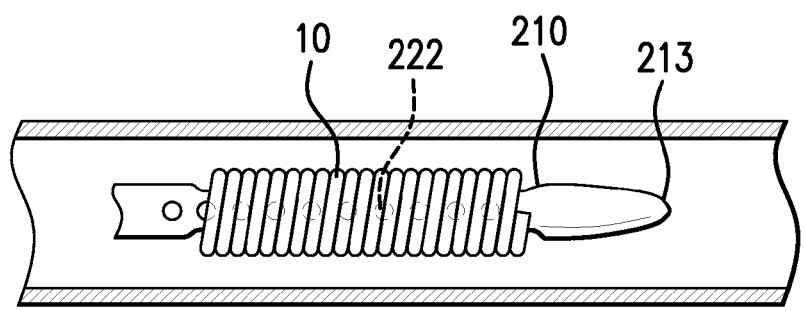
FIG. 13B is a side view of a device of the device of FIG. 13A positioned in the SI joint according to an embodiment of the present invention.
Figure 13C:
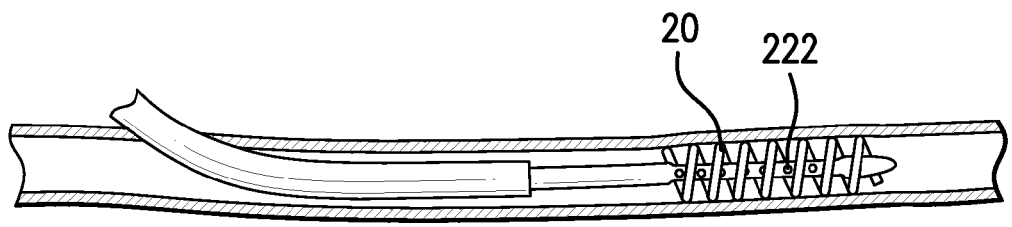
FIG. 13C is a side view of the device of FIG. 13B in an expanded state in the SI joint according to an embodiment of the present invention.
Figure 13D:
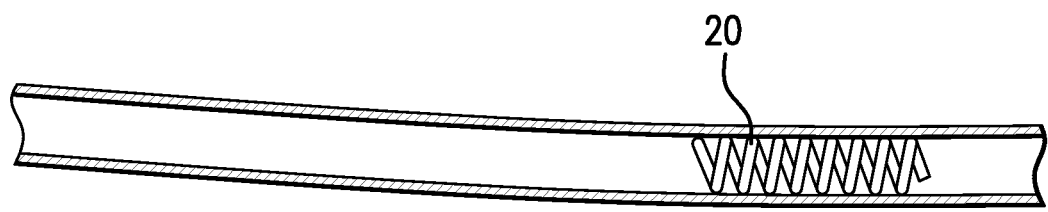
FIG. 13D is a side view of the device of FIG. 13C in an expanded deployed state in the SI joint after removal of the elongate member according to an embodiment of the present invention.

Referring to 13A-13D, in an exemplary use of device 10, the device is placed securely over an elongate member 210 having a threaded, pointed, cutting distal tip 213 with a closed distal end. Similar to the elongate member illustrated in FIG. 8, elongate member 210 in this embodiment can define a hollow channel along the longitudinal axis thereof as well as side apertures 222 similarly defined along the longitudinal axis thereof and in communication with the channel at one end and the outer surface of the elongate member at the other end. The side apertures 222 permit exit of fluid delivered through the elongate member. As stated above, distal tip 213 can have a closed end so that fluid only exits the side apertures. Device 10 can then be inserted into the SI joint as shown in FIG. 13A. Once at the proper position as seen in FIG. 13B, device 10 can be heated to a temperature at which the nitinol alloy from which body 20 is fabricated, reaches its transition temperature and austenite transformation occurs as seen in FIG. 13C. This can be accomplished by injecting a hot fluid through the channel of elongate member 210 to expandable body 20 so as to bathe and trigger expansion of device 10. Once device 10 is in a fully expanded state, the elongate member can be retracted leaving device 10 in place as shown in FIG. 13D. At any time during placement, a bone material can be inserted into cavity 25 of expandable body 20 or the outer surface of expandable body 20 can be pre-coated with a bone material. In either embodiment, the SI joint is exposed to bone material facilitating fusion of the joint.

Another method that can be used to deliver a device that is a self-expanding stent to the SI joint involves mounting the stent on the distal end of an elongate member and covering the stent with a surrounding sheath to maintain the stent in a compressed state. The self-expanding stent can be implanted by advancing the elongate member to the SI joint, withdrawing the sheath so that the stent can self-expand into the body lumen, and then withdrawing the elongate member and sheath leaving the stent implanted.

The expandable body of the device in this embodiment can have designs other than those described above, including designs that are common in the self-expanding stent field. For example, the expandable body can comprise flexible interwoven metal wires or small metal rings welded to adjacent rings. Each ring in such a design can have a zigzag configuration. Both the interwoven and multiple zigzag ring designs can be highly compressed to fit within a delivery sheath. Non-limiting examples of self-expanding stents that can be used in the present invention are described in U.S. Pat. No. 5,554,181 and U.S. Pat. No. 4,655,771, both of which are incorporated by reference herein.

The expandable body in this embodiment can be fabricated from a material commonly used in the manufacture of a self-expanding stent such as metals or polymers. Non-limiting examples of a metal are stainless steel, silver and a nickel titanium alloy. Non-limiting examples of polymers are polyesters, polyurethanes, polycarbonates, polysulfides, polypropylenes, polyethylenes, and polysulfonates. In preferred embodiments, the material is biodegradable.

In any of the above embodiments, any of the various described components can include a radio-opaque, such as, for example, barium, tungsten, bismuth, tantalum, and tin to allow the components to be visualized via standard imaging modalities.

Regarding the dimensions of devices used in the present invention, in most embodiments, the expandable bodies of the devices are generally from about 5 to 40 millimeters (mm) long and from about 5 to 20 mm wide in an unexpanded state. In a preferred embodiment, the expandable bodies are about 35 mm long and about 5 mm wide in an unexpanded state. In an expanded state, the expandable bodies are generally from about 5 to 40 mm long and from about 5 to 40 mm wide. In a preferred embodiment, the expandable bodies are 20 mm long and 20 mm wide in an expanded state.

The bone material used in the above described embodiments can be a bone graft material or a BMP. Bone graft materials are well known in the art and include both natural and synthetic materials. For example, the bone graft material can be an autologous or autograft, allograft, xenograft, or synthetic bone graft. BMPs are also well known in the art and include BMP-2, BMP-3, BMP-4, BMP-5, BMP-6 (VGR-1), BMP-7 (OP-1), BMP-8, BMP-9, BMP-10, BMP-11, BMP-12, BMP-13, BMP-14, BMP-15. Preferred BMPs are any of BMP-2, BMP-3, BMP-4, BMP-5, BMP-6, and BMP-7. The bone material can also include other therapeutic agents such as anti-microbial agents or antibiotics.

An exemplary surgical procedure to place a device of the present invention in the SI joint will now be described. The procedure can be performed in a minimally invasive fashion under fluoroscopy. The patient is placed in the prone position and a small stab incision is made in the posterior superior iliac spine directly underneath the visible dimples just above the buttocks over the sacroiliac joint. The SI joint is visualized under X-ray and a jam-sheaty needle is used to locate the area for placement. A guidewire (such as a K-wire) is advanced through the needle. The joint is opened and cartilage is cleared using a reamer or small channeling tool. The jam sheaty needle is removed and the guide wire is left in place. The device is inserted over the guide wire. Using a screwdriver or other driving tool, the device is inserted into the joint under fluoroscopy guided X-ray. When the ideal location is determined, the device is expanded under live fluoroscopy and stability checked. The device can be filled with a bone material prior to or after placement. The guide wire is removed and the small stab incision irrigated and closed. This procedure could also be preformed with an open larger incision.

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

We claim:

1. A method of stabilizing a sacroiliac joint in a patient in need thereof comprising:
   Providing a device comprising:
      a screw having a tip and a shaft, at least a portion of the shaft includes threads;
      an expandable body having a distal end, a proximal end and defining a cavity and at least one opening in communication with (i) the cavity and (ii) an outer surface of the body, and the expandable body being fitted over at least a portion of the shaft of the screw with the distal end of the expandable body capable of contacting the top of the screw;
      a nut member, the nut member capable of engaging the threads and capable of contacting the proximal end of the expandable body;
      the device having an unexpanded configuration in a non-deployed state and a radially expanded configuration in a deployed state;
   inserting the device into the sacroiliac joint; and
   radially expanding the expandable body to engage the sacroiliac joint to securely seat the device in the sacroiliac joint by rotating the nut member thereby compressing the expandable body between the tip and the nut member.

2. The method of claim 1, wherein the method further comprises placing a bone material on the expandable body such that the expandable body has an outer surface coated with the bone material.

3. The method of claim 1, wherein the at least one opening is a plurality of openings.

4. The method of claim 3, wherein the expandable body comprises a plurality of strips that extend from the proximal end to the distal end of the body, the plurality of strips defining the plurality of openings therebetween.

5. The method of claim 1, wherein the screw shaft has a proximal end and a distal end and, the tip is a pointed, cutting distal tip extending from the shaft, wherein the expandable body is mounted on the shaft.

6. The method of claim 5, wherein the shaft defines a channel extending from the proximal end to the distal end of the shaft.

7. The method of claim 5, wherein the screw is fabricated from a biodegradable material.

8. The method of claim 5, wherein the nut member is fabricated from a biodegradable material.

9. The method of claim 1, wherein the expandable body is fabricated from a biodegradable material.

10. The method of claim 1, wherein the device is inserted into the sacroiliac joint percutaneously.

11. The method of claim 1, further comprising placing a bone material within the cavity of the expandable body of the device to permit fusion of the sacroiliac joint.

12. The method of claim 11, wherein the bone material is a bone graft.

13. The method of claim 11, wherein the bone material is a bone morphogenetic protein.

* * * * *